United States Patent [19]

Warncke et al.

[11] 4,341,108
[45] Jul. 27, 1982

[54] MASS FLOW-DEPENDENT GAS ANALYZER WITH THROUGH-FLOW CONTROL DURING LOW PRESSURE OPERATION

[75] Inventors: Heinz Warncke, Cologne; Melchior Kahl, Bergisch Gladbach; Hans H. Meyer, Dormagen; Paul Schürmeyer, Neuss, all of Fed. Rep. of Germany

[73] Assignee: Bayer Aktiengesellschaft, Leverkusen, Fed. Rep. of Germany

[21] Appl. No.: 176,373

[22] Filed: Aug. 8, 1980

[30] Foreign Application Priority Data

Aug. 10, 1979 [DE] Fed. Rep. of Germany ....... 2932436

[51] Int. Cl.³ .............................................. G01N 27/16
[52] U.S. Cl. ............................................. 73/23; 422/54
[58] Field of Search ................. 73/23; 422/54, 83, 93; 23/232 R

[56] References Cited

U.S. PATENT DOCUMENTS 3,763,877 10/1973 Lieb ..................................... 422/54
4,038,864 10/1977 Cooper et al. ......................... 73/23

Primary Examiner—Stephen A. Kreitman
Attorney, Agent, or Firm—Sprung, Horn, Kramer & Woods

[57] ABSTRACT

By means of a suction pump located at the outlet of the analyzer device and a combination of choke members connected in parallel in a row and respective low pressure controllers at the outlet of the gas analyzer and at the connection point of the series connection and parallel connection of the choke members, a constant sample flow through the analyzer is produced. Thus, even where there is a fluctuating measuring gas pressure and a variable flow resistance in the inlet part of the gas analyzer, the proportionality of the measuring signal to the concentration of the measuring component is ensured.

6 Claims, 2 Drawing Figures

4,341,108

MASS FLOW-DEPENDENT GAS ANALYZER WITH THROUGH-FLOW CONTROL DURING LOW PRESSURE OPERATION

BACKGROUND OF THE INVENTION

The present invention relates to continuously operating, particularly heated, gas analysers comprising a mass flow-dependent detector, which must be (a) operated under low pressure because the measuring gas is not present under sufficient excess pressure and because no suitable temperature-resistant or corrosion-proof pumps may be used upstream of the analyser, and (b) charged with one or more gas flows apart from with the measuring gas, as this is required for its function.

For this purpose, a suction device is usually positioned at the outlet of the detector which maintains the low pressure constant with respect to atmospheric pressure. The amount of measuring gas which is supplied is adjusted to a specific value by connecting a choke upstream of the detector.

In order to improve the time behaviour, a by-pass is often connected parallel to the detector which contains another choke determining the by-pass flow. However, in this arrangement, a constant mass flow of the measuring gas is only ensured when the pressure of the measuring gas is constant at its inlet.

Continuous flame ionization detectors (FID) and the thermionic detectors based on a similar effect produce a measuring signal which is proportional to the mass flow. For this reason, a constant mass flow of measuring gas has to be metered into the detector. Metering the measuring gas usually involves compressing the measuring gas by means of a pump upstream of the detector to a pressure which is adjusted by a pressure control apparatus to a constant excess pressure with respect to atmospheric pressure and which is connected to the inlet of the detector, operated at atmospheric pressure, via a fixed choke member. In this way, a constant flow of measuring gas is adjusted due to the constant differential pressure at the choke member. This control of the mass flow upstream of the detector has the advantage that it is not influenced by the addition of other gas flows into the detector (which are required for its function, e.g. fuel gas and combustion air for the FID). Any gas compressor which does not change the composition of the measuring gas may be used as the pump. Pumps with mechanically moving parts, e.g. diaphragm pumps, are usually used as the pumps. Overflow controllers (back pressure controllers) are usually used as the pressure control apparatus which allow a variable partial flow of the measuring gas to flow away into the atmosphere through a by-pass line by means of a variable choke. Needle valves, capillaries or nozzles may be used as choke members in the inlet of the detector. The type of measuring gas metering which has been described has proved to be useful in continuous FID devices in the field of emission measurement, in which devices the measuring gas is present as relatively clean air. For uses in the field of emission measurement, this type of metering has considerable disadvantages which derive from the following circumstances with high loads of the measuring gases:

(a) the dew point of the measuring gas may lie considerably above the ambient temperature, and (b) the measuring gas may have a heavily corrosive effect.

For these reasons, it has proved to be necessary with emission measuring devices to heat all components which come into contact with the measuring gas to temperatures of from 150° to 200° C. However, the disadvantage of heating the measuring gas system to such high temperatures is that the life of some components, such as pumps and pressure controllers, is drastically reduced to a level which is not acceptable.

This can be remedied by using a detector which operates in connection with a low pressure control during suction operation. An apparatus constructed according to this principle is described for example in the article by H. Fischer et al. in GIT March 1974 p. 214–219. The low pressure is controlled in this case by a differential pressure controller which maintains the differential pressure at the outlet of the detector constant with respect to atmospheric pressure. Adjusting the quantity of measuring gas supplied to the detector and thereby adapting the measuring sensitivity to the respective problem to be solved is effected by a capillary which is connected upstream of the detector. A by-pass line bridging the detector which opens out upstream of the capillary and contains another capillary is used to improve the time behaviour of the arrangement. An equalizing reservoir is positioned at the outlet of the detector, the suction device being connected thereto on one side and the differential pressure controller on the other side.

The disadvantage of this apparatus is that it is basically unsuitable for a fluctuating measuring gas pressure. Only the differential pressure between the surrounding air and the equalizing reservoir is maintained constant by the low pressure control. However, pressure fluctuations in the measuring gas and the change in the mass flow of the measuring component, resulting therefrom, cannot be eliminated and result in a systematic error in the reading. The same applies to changes in the flow resistance between the inlet and the detector (e.g. when an inlet filter is soiled).

SUMMARY OF THE INVENTION

The object of the invention is to ensure the proportionality of the measuring signal to the concentration of the measuring component in a mass flow-dependent analyser, which operates under suction operation on the principle of the low pressure control described above at the outset, even with a fluctuating measuring gas pressure and varying flow resistance in the inlet part. For this purpose, the mass flow of the measuring gas must be maintained constant through the detector. However, the mass flow only remains constant when the absolute pressure in the detector and the volumetric flow of the measuring gas through the detector are simultaneously maintained constant.

It is sufficient to disregard the known fluctuations of the barometric pressure and maintain the low pressure in the detector constant with respect to atmospheric pressure rather than absolute pressure.

The basis for achieving the above stated object is a gas analyser comprising a mass flow-dependent detector with the following features which have already been mentioned:

(a) a suction device at the detector outlet;

(b) a low pressure controller, which is connected to the output of the detector and which maintains the low pressure $p_3$, produced by the suction device, at the output of the detector constant with respect to the atmospheric pressure $p_0$;

(c) a first choke which is connected upstream of the detector in the measuring gas line; and (d) a second choke which is connected parallel to the series connection of the first choke and detector as a by-pass.

Achieving the object according to the invention is now characterised in that a third choke is connected upstream of the common gas entry into the first and second choke and another low pressure controller is connected to the common connection point of the three chokes, which low pressure controller sucks in air under atmospheric pressure at its inlet and maintains its outlet pressure $p_2$ constant as a difference with respect to atmospheric pressure $p_0$ by changing this quantity of air, the second choke being a necessary component of the other low pressure control. In this way, the pressure $p_2$ at the connection point of the three chokes is adjusted to an absolute value which is clearly above the pressure $p_3$ in the detector and below the lowest pressure of the measuring gas.

In order to avoid soling having an effect on the low pressure control, the flow of air flowing through the by-pass is not adjusted by a variable choke member, but exclusively via the transporting capacity of the suction device. Moreover, the transporting capacity of the suction device is preferably adjusted such that the quantity of air sucked up by the low pressure controller located at the outlet of the detector is as large as the total of the mass flows in the detector outlet and the by-pass.

The essential advantage of the invention resides in the fact that by using simple devices, a constant sample flow is achieved through the detector so that the proportionality of the measuring signal to the concentration of the measuring component is obtained even when the measuring gas pressure fluctuates within certain limits or the flow resistance in the inlet part changes. Other advantages are the wide variety of applications and the long life and low maintenance costs. This is largely because only clean air and not contaminated or corrosive measuring gas flow through both low pressure controllers. Furthermore, the new measuring system allows an anti-explosion construction (e.g. of a flame ionization detector) to be formed in a simple way. In contrast to designs comprising measuring gas pumps upstream of the detector, the invention has the particular advantage of a substantially smaller dead volume upstream of the detector. In this way, not only is a more favourable dead time achieved but also a reduction in the volume of all parts guiding the measuring gas so that they may be installed in a smaller space, e.g. in the detector furnace.

An embodiment of the invention is explained in more detail below with reference to drawings.

DETAILED DESCRIPTION OF THE INVENTION

Figure 1:
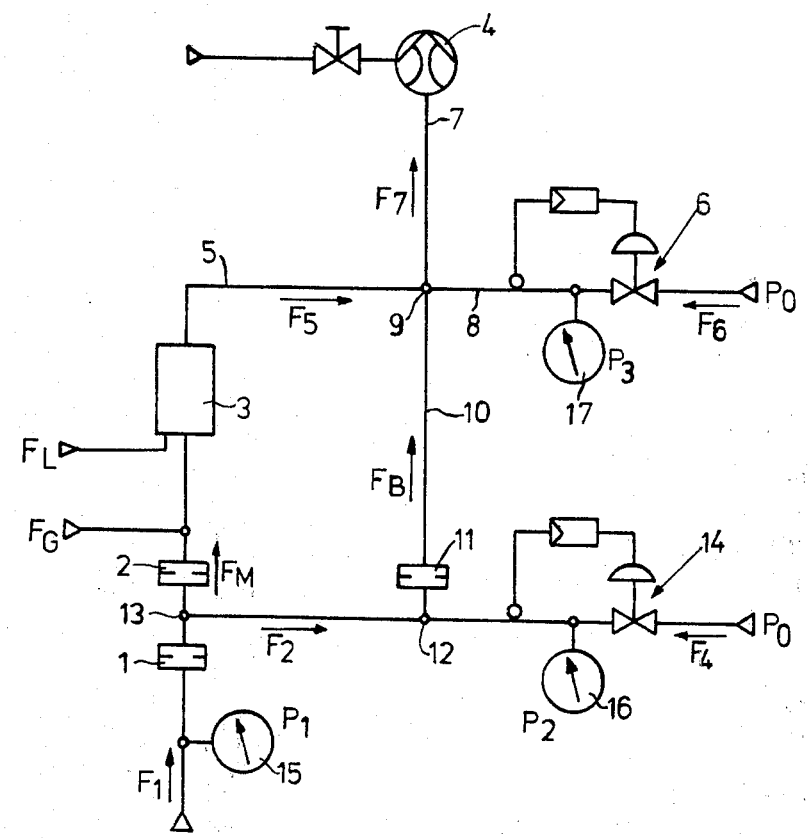
FIG. 1 shows a simplified block diagram to explain the control principle.

According to FIG. 1, the measuring gas to be analysed which is under the supply pressure $p_1$ is fed into the detector 3 via a series connection of two fixed chokes 1 and 2. The choke 1 is connected to the measuring gas and the choke 2 is connected to the detector 3. The detector may, for example, be a flame ionization detector or a thermionic detector. The outlet of the detector 3 is connected to the suction side of an injector 4. The outlet line 5 and thus the detector 3 are brought to a pressure $p_3$ which is clearly lower than atmospheric pressure $p_0$, which pressure $p_3$ is maintained constant with respect to $p_0$:

$$p_0 - p_3 = CONSTANT$$

This is effected using an overflow controller 6, acting as a low pressure controller, by which air under atmospheric pressure is sucked up from outside for the purpose of control. The detector output line 5, the suction line 7 of the injector 4 and the outlet 8 of the overflow controller 6 are connected to a cross-piece 9 to whose fourth line 10 is connected another choke 11 which leads via two T-pieces 12 and 13 to the connection line between the chokes 1 and 2 at the detector inlet. The operation of the low pressure controller 6 corresponds to that of an immersion flask whose immersion tube was open towards the atmosphere while the connection of the gas volume was connected to the cross-piece 9.

A second similar low pressure controller 14 is connected to the third support of the T-piece 12, by which air under atmospheric pressure $p_0$ is also sucked in by the injector 4 via the choke 11. Thus, the pressure at the connection point 13 between the chokes 1 and 2 connected in series is adjusted to a pressure $p_2$ which is maintained at a value lower than $p_0$ by a constant amount:

$$p_0 - p_2 = CONSTANT$$

The set values of $p_2$ and $p_3$ are adjusted so that $p_2$ is clearly (approximately 100 mbar) above $p_3$, but also below the minimum value of $p_1$. Manometers 15,16 and 17 are provided in the individual branches to measure the pressure.

The T-pieces 12 and 13 therefore constitute the common connection point of the three chokes 1,2 and 11. The line 10 with the choke 11 forms a by-pass which is connected parallel to the series connection of detector 3 and choke 2. The measuring gas flow $F_1$ is divided into two partial flows at the T-piece 13. One part $F_M$ flows through the detector and the other part $F_2$ flows to the T-piece 12 and there unites with the air flow $F_4$ sucked up by the controller 14. The two partial flows $F_2 + F_4$ form the by-pass flow $F_B$ which is united at the junction 9 with the partial flow $F_5$ coming from the detector 3, which partial flow $F_5$ consists of the burnt mixture of the partial flow $F_M$, the fuel gas flow $F_G$ and the combustion air flow $F_L$, and with the air flow $F_6$ sucked up by the controller 6. The total $F_7$ of these partial flows is sucked off by the injector 4.

When designing the chokes 1, 2 and 11, the following points of view should be taken into account:

1. The flow resistance of the choke 1 is chosen such that at the lowest occurring supply pressure $p_1$, the differential pressure $p_1 - p_2$ at the choke 1 still produces a sufficiently high total of the measuring gas flow $F_M$ and the by-pass flow $F_2$.

2. The flow resistance of the choke 2 is chosen such that the differential pressure $p_2 - p_3$ at the choke 2 produces the required measuring gas flow $F_M$ by the FID 3.

The flow resistance of the FID is much smaller than that of choke 2 and may thus be disregarded.

3. The choke 11 is designed so that the differential pressure $p_2-p_3$ at the choke 11 produces a by-pass flow $F_B$, which is approximately double the partial flow $F_2$ in a normal case. The difference of $F_B$ and $F_2$ is then sucked up by the controller 14 as air flow $F_4$.

4. The suction capacity of the pump or injector 4 is adjusted so that the quantity of air $F_6$ sucked up by the controller 6 is as large as the total of the outlet flow $F_5$ of the detector and the by-pass flow $F_B$.

During operation, the measuring gas flow $F_1$ flowing in through the choke 1 is divided into a mostly smaller partial flow $F_M$ to the detector 3 and a mostly larger partial flow $F_2$ flowing to the by-pass, which is united with the air flow $F_4$ sucked up by the controller 14 to the by-pass flow $F_B$. The by-pass flow $F_B$ is united in the cross-piece 9 with the waste gas $F_5$ of the detector 3 and with the air flow $F_6$ through the controller 6. If the measuring gas pressure $p_1$ is reduced, $p_1-p_2$ becomes smaller. Thereby, the by-pass flow portion $F_2$ is reduced by the choke 11. By increasing its quantity of air $F_4$, the controller 14 ensures that $F_B$ and thereby the fall in pressure $p_2-p_3$ remains constant at the choke 11. Conversely, with an increase in measuring gas pressure $p_1$, the difference $p_1-p_2$ is also increased. Consequently, the by-pass flow portion $F_2$ is increased by the choke 11 while the admixed flow of air $F_4$ is correspondingly reduced by the controller 14. Where $F_4=0$, the upper admissible limit of the measuring gas pressure $p_1$ is thereby attained. The lower limit of $p_1$ is determined by the by-pass flow portion $F_2$ being 0. In this case, only the quantity $F_M$, required for the detector, would still be sucked up and the dead time would be correspondingly increased. With a further reduction of $p_1$, the measuring gas at the T-piece 13 would be diluted with air from the controller 14, resulting in falsification of the measuring gas flow. It follows from $p_0-p_3=$ constant and $p_0-p_2=$ constant that $p_2-p_3=$ constant, so that the conditions are met for the low pressure in the detector to remain constant with respect to atmospheric pressure and for the volumetric flow of the measuring gas through the detector to remain constant.

A complete independence from atmospheric pressure would be achieved if the absolute values of $p_2$ and $p_3$ were maintained constant by absolute pressure controllers. When designing the chokes and controllers, the fluctuation range of the absolute value of $p_1$ would then have to be considered. This means that the fluctuation of $p_0$ is added to the fluctuation of $p_1-p_0$ so that the fluctuation width of $p_1$ to be compensated by the control apparatus is correspondingly larger.

Figure 2:
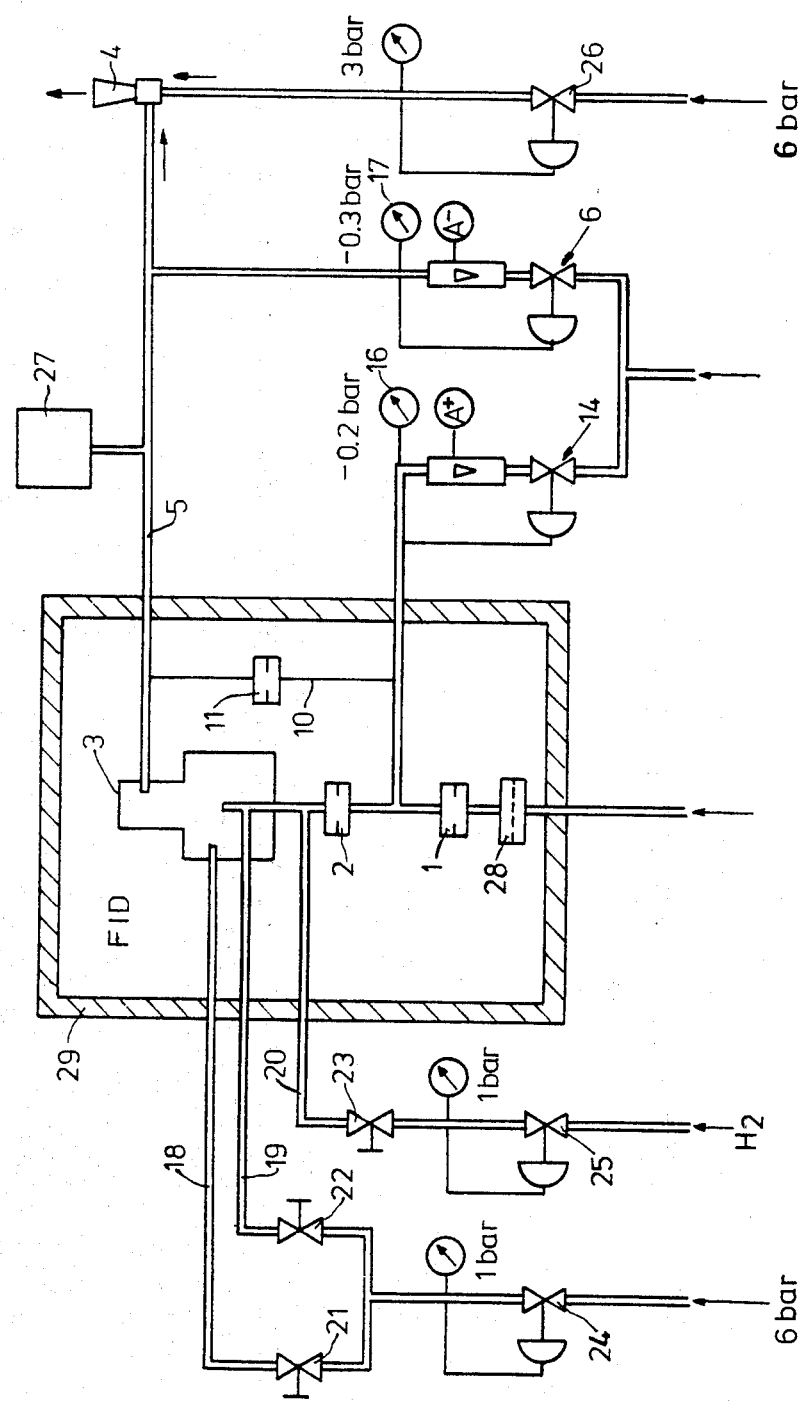
FIG. 2 shows a complete block diagram for an FID operated under low pressure, including the relevant control devices.

FIG. 2 shows a practical embodiment of the invention. In this Figure, the supply 19 used for oxygen compensation and the adjusting members 21,22,23,24 and 25 for the burning process in the FID 3 are also shown. The inlet pressure of the combustion air (upstream of the valves 21 and 22) also of the fuel gas (hydrogen) is adjusted to a value of 1 bar.

The blowing gas for the injector 4 is taken, like the combustion air for the FID, from an instrument air network. The suction capacity of the injector is adjusted using the pressure controller 26. The instrument air pressure of 6 bars is reduced in this case to approximately 3 bars. The outlet line 5 of the FID 3 is connected to a buffer volume 27. As a result of this, flow fluctuations are absorbed which could otherwise cause a disturbing flickering in the FID.

The chokes 1,2 and 11 consist in practice of special steel capillaries or nozzles. The FID 3, all the chokes, the by-pass 10 and a filter 28 which is additionally connected in the measuring gas line are housed in a thermostatic furnace 29. Thus, constant flow conditions are ensured, and condensation and consequent corrosion in the parts through which the measuring gas flows are avoided.

The controller 14 is adjusted according to the flow resistances of the chokes 1,2 and 11 such that the pressure $p_2$ at the common connection point of the three chokes is $-0.2$ bar, while at the outlet of the FID, a low pressure of $-0.3$ bar is adjusted using the controller 6. The operation of both the similar overflow controllers 6 and 14 is based on the fact that air is sucked up to a lesser or greater extent from the atmospheric side and flows into the system. Therefore, the measuring gas never flows through either controllers so that no corrosive damage may occur.

Under the conditions stated above, an interval of $+0.1$ bar to $-0.1$ bar resulted as the most admissible fluctuation of $p_1-p_0$. Including the barometric fluctuations, a fluctuation range of $+0.12$ bar to $-0.12$ bar is thereby produced for the absolute value of the supply pressure $p_1$.

We claim:

1. In a continuously operated gas analyser comprising a mass flow-dependent detector, consisting of:
   (a) a suction device at the detector outlet;
   (b) a low pressure controller connected to the detector outlet, which controller maintains the low pressure $p_3$, produced by the suction device, constant at the detector outlet with respect to the atmospheric pressure $P_0$;
   (c) a first choke which is connected upstream of the detector in the measuring gas line; and
   (d) a second choke which is connected parallel to the series connection of the first choke and the detector as a by-pass,
   the improvement comprising: a third choke connected upstream of the common gas entry into the first choke and the second choke and low pressure control means connected to the common connection point of the three chokes and including the second choke for sucking up air under atmospheric pressure at its inlet and maintaining its outlet pressure $p_2$ at a value which has a constant difference from the atmospheric pressure $P_0$.

2. In a process for continuously analyzing of the type wherein a mass flow-dependent detector is provided having
   (a) a suction device at the detector outlet;
   (b) a low pressure controller connected to the detector outlet, which controller maintains the low pressure $p_3$, produced by the suction device, constant at the detector outlet with respect to the atmospheric pressure $p_0$;
   (c) a first choke which is connected upstream of the detector in the measuring gas line; and
   (d) a second choke which is connected parallel to the series connection of the first choke and the detector as a by-pass;
   the improvement comprising: connecting a third choke upstream of the common gas entry into the first choke and the second choke and connecting another low pressure controller including the second choke to the common connection point of the three chokes to suck up air under atmospheric pressure at its inlet and maintain its outlet pressure $p_2$ at a value which has a constant difference from the atmospheric pressure $p_0$ by changing this quantity of air.

3. A method according to claim 2, wherein the pressure $p_2$ at the connection point of the three chokes is adjusted to a value which is clearly above the pressure $p_3$ in the detector and below the lowest pressure of the prevailing measuring gas.

4. A method according to claim 3, wherein the flow of air flowing through the by-pass is only adjusted via the transporting capacity of the suction device.

5. A method according to claim 4, wherein the three chokes are designed such that the flow of air $F_4$ sucked in by the low pressure controller positioned at the common branching point of these chokes is approximately the same as the total measuring gas flow $F_1$ with an average measuring gas pressure $p_1$.

6. A method according to claim 5, wherein the transporting capacity of the suction device is adjusted such that the flow of air $F_6$ sucked up by the low pressure controller located at the detector outlet is approximately the same as the total of the mass flows in the detector outlet ($F_5$) and the by-pass ($F_B$).

* * * * *